United States Patent [19]

Olij

[11] Patent Number: Plant 7,137

[45] Date of Patent: Feb. 6, 1990

[54] ROSE PLANT — OLIJCHOU VARIETY

[75] Inventor: Huibert W. Olij, De Kwakel, Netherlands

[73] Assignee: The Conard-Pyle Company, West Grove, Pa.

[21] Appl. No.: 301,109

[22] Filed: Jan. 25, 1989

[51] Int. Cl.[4] ..... A01H 5/00

[52] U.S. Cl. ..... Plt./15

[58] Field of Search ..... Plt./15

*Primary Examiner*—James R. Feyrer

*Attorney, Agent, or Firm*—Burns, Doane, Swecker & Mathis

[57] ABSTRACT

A new and distinct variety of Intermediate rose plant is provided which abundantly forms attractive semi-double yellow blossoms. These blossoms are lemon yellow in coloration and are suffused with marigold orange on the edges. Such blossoms are long lasting. The plant exhibits vigorous vegetation and is well suited for cut flower production. Additionally, the plant is not particularly affected by cryptogamic diseases.

1 Drawing Sheet

SUMMARY OF THE INVENTION

The new variety of Intermediate rose plant was created by artificial pollination wherein two parents were crossed which previously had been studied in the hope that they would contribute the desired characteristics. The female parent (i.e., the seed parent) of the new variety was the Dr. Verhage variety (nonpatented in the United States). The male parent (i.e., the pollen parent) was an unnamed seedling (nonpatented in the United States). The parentage of the new variety can be summarized as follows:

[Dr. Verhage x Unnamed Seedling].

The seeds resulting from the above pollination were sown and small plants were obtained which were physically and biologically different from each other. Selective study resulted in the identification of a single plant of the new variety.

It was found that the new variety of Intermediate rose plant of the present invention possesses the following combination of characteristics:

(a) forms in abundance attractive long lasting semi-double lemon yellow blossoms which are suffused with marigold orange on the edges,
(b) is well adapted for greenhouse forcing,
(c) exhibits vigorous vegetation, and
(d) is particularly suited for cut flower production.

The blossom coloration is strong and stable, and the blossoms exhibit a good form when open.

The new variety well meets the needs of the horticultural industry for all uses and is particularly well suited for cut flower production.

The new variety has been found to undergo asexual propagation by a number of routes, including budding, grafting, cuttage, etc. The characteristics of the new variety have been found to be strictly transmissible by such asexual propagation from one generation to another.

The new variety has been named the Olijchou variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were three years of age and were observed during January while budded on *Rosa indicia* and growing in a greenhouse at Cap d'Antibes, France.

DETAILED DESCRIPTION

Figures 1, 2, 3, 4, 5, 6, 7, 8, 9, 10, 11, 12, 13, 14, 15, 16, 17:
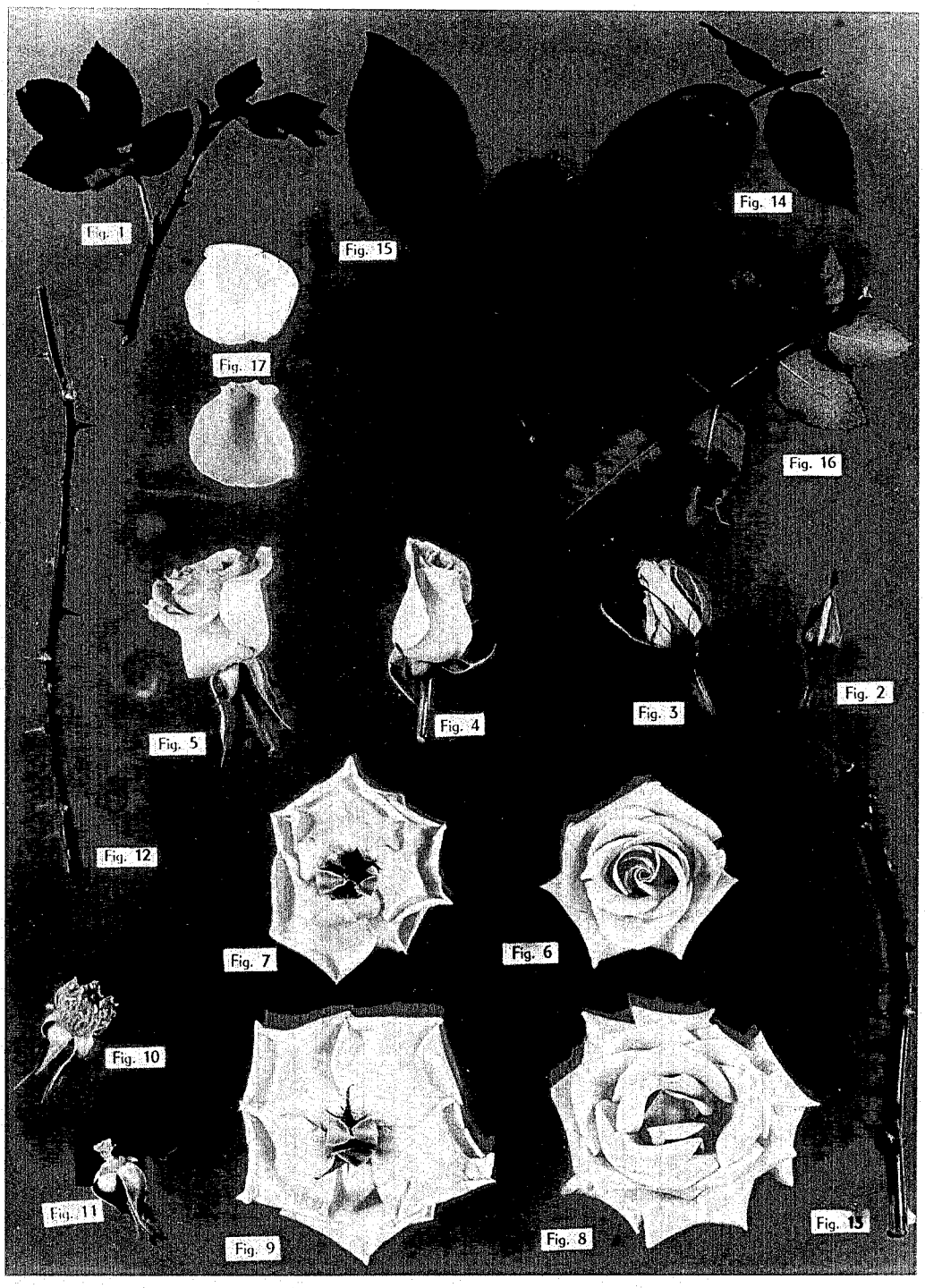
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — upper surface.
FIG. 16 illustrates a specimen of a leaf with seven leaflets — plan view — under surface.
FIG. 17 illustrates specimens of two petals with the under surface being shown on the top and the upper surface on the bottom.

The chart used in the identification of the colors is that of The Royal Horticultural Society (R.H.S. Colour Chart). The description is based on three year old plants made during January while budded on *Rosa indicia* understock and growing in a greenhouse at Cap d'Antibes, France. The coloration in common terms precedes reference to the chart.

Class: Hybrid tea.

Plant:

*Height.*—Plants were pruned to a height of 85 cm. produce floral stems having a length of approximately 30 to 60 cm.

*Habit.*—Upright.

Branches:

*Color.*—Young stems: bronze green, Yellow-Green Group 146A, widely stained with reddish brown. Adult wood: medium green, Green Group 136B.

*Thorns.*—Size: medium to large. Quantity: average. Color: greenish-pinkish on young stems and brown on mature wood.

Leaves:

*Stipules.*—Adnate, pectinate, very wide and serrated.

*Petioles.*—Upper surface: striped reddish brown on young foliage and medium green on adult foliage with glandular edges. Under surface: medium green, bear a few very thin and crooked prickles.

*Leaflets.*—Number: 3, 5 and 7 (most often). Shape: spear-shaped. Serration: simple and regular. Texture: consistent. General appearance: bright and ample foliage. Color (young foliage): upper surface: medium green, Green Group 143A, widely stained reddish brown. Under surface: reddish brown. Color (adult foliage): upper surface: dark green, Green Group 139A. Under surface: light green, Green Group 137C.

Inflorescence:

*Number of flowers.*—Generally one per stem.

*Peduncle.*—Upright, rigid, medium green in coloration, and bears very narrow prickles on the lower half. The length is approximately 8 to 9 cm. on average.

*Sepals.*—Upper surface: tomentose, greenish in coloration. Under surface: smooth, light green in coloration, the edges of the outer sepals are only slightly appendiculated.

*Buds.*—Shape: egg-shaped. Length: approximately 2.5 to 3 cm. on average. Size: medium. Color upon opening: upper surface: lemon yellow, Yellow-Orange Group 14A, and widely edged with marigold orange, Orange Group 28B. Under surface: light Indian yellow, Yellow-Orange Group 17C and very slightly tinted on the edges of the petals with marigold orange, Orange Group 28B.

*Flower.*—Shape: cup-like and semi-double. Diameter: approximately 10 to 12 cm on average. Color (when opening begins: upper surface: light lemon yellow, Yellow-Orange Group 14C, suffused with marigold orange, Orange Group 28B. Under surface: light lemon yellow, Yellow Group 13B. Color (when blooming): upper surface: lemon yellow, Yellow-Orange Group 14A, suffused with light marigold orange, Orange Group 28B. Under surface: straw yellow, Yellow Group 13C. Color (at end of opening): upper surface: light lemon yellow, Yellow-Orange Group 14C, suffused with pale marigold orange, Orange Group 28B. Under surface: straw yellow, Yellow Group 13C. Fragrance: slight. Lasting quality: long. Petal number: approximately 20 to 23 on average plus 2 to 3 petaloids commonly are present. Texture: consistent. Petal drop: good. Stamen number: approximately 141 to 146 on average. Anthers: normal, yellowish in coloration and edged with ochre. Filaments: bright yellow, of irregular heights. Pistils: approximately 66 to 70 on average. Stigmas: normal, bright yellow. Styles: straw colored with fuchsine tips, tomentose, bonded at the base, of irregular heights. Receptacle: smooth, medium green, in longitudinal section it is in the shape of a pitcher.

Development:

*Vegetation.*—Vigorous.

*Blooming.*—Very abundant.

*Resistance to diseases.*—Good.

*Aptitude to forcing.*—Excellent.

I claim:

1. A new and distinct variety of Intermediate rose plant characterized by the following combination of characteristics:

(a) forms in abundance attractive long lasting semi-double lemon yellow blossoms which are suffused with marigold orange on the edges, (b) is well adapted for greenhouse forcing, (c) exhibits vigorous vegetation, and (d) is particularly suited for cut flower production;

substantially as herein shown and described.

* * * * *